United States Patent
Steinborn et al.

[11] Patent Number: 6,080,421
[45] Date of Patent: Jun. 27, 2000

[54] TRANSDERMAL THERAPEUTIC SYSTEM IDENTIFIED WITHOUT PRINTING INKS

[75] Inventors: Peter Steinborn; Michael Horstmann, both of Neuwied, Germany

[73] Assignee: LTS Lohmann Therapie-Systeme GmbH, Neuwied, Germany

[21] Appl. No.: 08/981,133

[22] PCT Filed: Apr. 23, 1996

[86] PCT No.: PCT/DE96/00699

§ 371 Date: May 15, 1998

§ 102(e) Date: May 15, 1998

[87] PCT Pub. No.: WO96/38187

PCT Pub. Date: Dec. 5, 1996

[30] Foreign Application Priority Data

May 29, 1995 [DE] Germany ............................ 195 19 593

[51] Int. Cl.[7] .............................. A61K 9/70; A61F 13/00; A61L 15/03
[52] U.S. Cl. ........................... 424/449; 424/448; 424/447
[58] Field of Search ................................... 424/447, 448, 424/449

[56] References Cited

U.S. PATENT DOCUMENTS

| | | | |
|---|---|---|---|
| 4,359,442 | 11/1982 | Cleminson et al. | 264/280 |
| 4,758,434 | 7/1988 | Kydonieus | 424/449 |
| 5,443,727 | 8/1995 | Gagnon | 210/490 |
| 5,593,395 | 1/1997 | Martz | 604/304 |

OTHER PUBLICATIONS

Chien, Development of Transdermal Controlled Release Delivery Systems: An Overview: Transdermal Delivery of Drugs.

Volumn I, Edited by Kydonieus et al., CRC Press Inc., Boca Raton, Florida, Chapter 7, pp. 81–100 (Nov. 30, 1986.

*Primary Examiner*—Thurman K. Page
*Assistant Examiner*—Brian K. Seidleck
*Attorney, Agent, or Firm*—Wenderoth, Lind & Ponack, L.L.P.

[57] ABSTRACT

The invention refers to a transdermal therapeutic system for the delivery of active agents to the human body.

The backing layer consists of common pharmaceutical plastic layer laminates which require labeling, e.g. by printing. The problem to solve lies in toxicological, technological and drug law disadvantages of pigment- or varnish-printing.

According to the invention, the coding does not consist of an ink- or pigment layer but in an effect on surface properties of the backing layer corresponding to the coding.

2 Claims, 1 Drawing Sheet

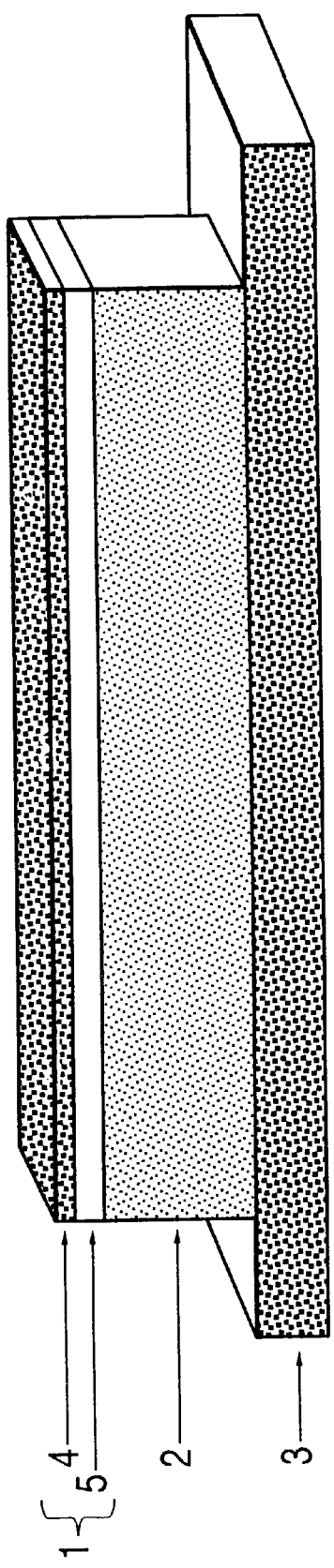

ND RANSDERMAL THERAPEUTIC SYSTEM IDENTIFIED WITHOUT PRINTING INKS

This application is a 371 of PCT/DE96/00699, filed Apr. 23, 1996.

DESCRIPTION

BACKGROUND OF THE INVENTION

The invention relates to a transdermal therapeutic system for delivering active agents to the human body through the skin.

Transdermal therapeutic systems have already been introduced in the market for the pharmaceutical treatment of a number of diseases and have proven themselves in practice.

Moreover, a number of different possible system designs are known in the art (see for example Y. W. Chien in: A. F. Kydonieus and B. Berner (eds.) "Transdermal Delivery of Drugs", p. 81–100).

There are some fundamental similarities, however, independent of the variety of possible system designs between the systems known in the art these similarities are:

1. For protection against unwanted delivery of the active agent or skin moisture by the transdermal therapeutic system and also for protection against adhesion to textiles, an essentially impermeable, non-sticking backing layer (1) is used.

2. Since transdermal therapeutic systems have to stick on the skin, the layer facing the skin, and occasionally only a part of the area facing the skin is made from a pressure-sensitive adhesive.

3. Because of these self-adhesive qualities, a removable protective layer (3) made from a non-adhesive material, if necessary, is added to the transdermal therapeutic system.

The backing layer consists of the usual pharmaceutical materials, such as plastic webs, papers, nonwovens or textiles. Frequently, thermoplastic plastics are used because of their easy processability, such as extruding or casting, stretching along the length or cross in the case of films or also in form of fibers in their use as non-woven-like or textile applications.

Specifically suited plastics are exemplified by polyethylene terephthalate (PETP) and other polyesters, polyethylene (HDPE or LDPE), polyvinyl chloride (PVC, optional softenized), ethylene-vinyl acetate-copolymers (EVA) and polypropylene (PP). In order to combine advantageous features, laminates can be used (for example EVA or PE (outer surface) and PETP). The surface (4) can be (PE or EVA) equipped with skin-like soft "touch" and on the other side, a PETP layer (5) may act as a diffusion barrier against the active substance of the transdermal therapeutic system.

Similarly, as in the case of conventional pharmaceutical application forms, the marketing companies, the regulatory agencies or consumer organizations wish or even require the clear identification of the systems. In this way, a positive identification of the product is necessary when the package leaflet and other accompanying information is not available. Form, size and appearance alone cannot ensure positive identification.

It has become therefore conventional in the art to print such systems with a suitable printing ink on the outside of the backing layer. This possibility, described in EP 0 114 125, allows easy identification and makes colored noticeable features possible.

Furthermore, it is known by those skilled in the plastics art that thermoplastic plastics are deformable under heat and a change of shape may be used to emboss patterns or information on everyday commodities, and also on plastic laminates (see e.g., U.S. Pat. No. 4,359,442).

For the labeling of articles, especially in the packing of pharmaceutical products, however, only transfer printing is usually used in which a pigmented plastic laminate is pressed for a short period of time against the matter to be printed. This allows the ink pigment to be applied onto the substrate.

Also embossing is known as a procedure to label transdermal therapeutic systems (DE-Gbm 94 9 784). Here, a sheet-like means of labeling with embossments or prints are applied on the drug-containing part of patches containing pharmaceutical agents.

This state of the art nevertheless has a number of disadvantages: with the use of (only toxicologically acceptable) printing inks, to work with solvent-containing carrier fluids for pigments and varnishes at the place of the manufacture of pharmaceutical products is problematic because of possible contamination with foreign materials.

A number of varnishes do not or only insufficiently stick on the backing material; this way only printable materials are suitable.

The printing ink on the transdermal therapeutic systems may soften during storage and the imprint becomes unreadable upon the influence of volatile agents in the transdermal therapeutic system.

Furthermore, a color print code on the transdermal therapeutic system is disturbing cosmetically for the consumer.

If, as in DE-Gbm 94 9 784, embossing is chosen for application of the coding, at application of ordinary techniques accessible for those skilled in the art, the drug-containing part has to be exposed to an undue and high pressure, noxious for the pharmaceutical form of application.

Compression of the matrix in this way easily leads to local changes of the function of the patch, particularly the release in vitro. An embossment performed prior to application of a sheet-like carrier of label requires a second pressure sensitive adhesive intermediate layer which usually leads to a bubble-containing unattractive appearance.

The embossment mentioned in DE-Gbm 94 09 784 is not described technically more precisely in the detail there. The use of a backing made of a uniform polymer material, which is the predominant use, an embossment, in any way performed, with or without the action of heat, causes the production of "thin areas". This may destroy the barrier property of the backing for the active agent and obviously, for this reason, embossing is not done in practice.

SUMMARY OF THE INVENTION

The task of the present invention is, therefore, a transdermal therapeutic system consisting of a backing layer of thermoplastic material consisting of a laminate of a low-melting thermoplastic material on the external surface and a higher melting thermoplastic material facing the skin side, and a persistent, identifying code applied on this laminate, as well as an active part containing the active agent, which allows a safe labeling on said backing layer without the use of further additives.

According to this invention, the task is settled by the fact that this coding consists of a locally different surface property, surface thickness or surface roughness.

The advantages of this invention are observed particularly with active agents or other ingredients which are volatile at the storage temperature and, therefore, may migrate through the gas space of the transdermal therapeutic system according to the state of the art.

DETAILED DESCRIPTION OF THE INVENTION

Such substances are nicotine, nitroglycerine, for example, are examples of pharmaceutical agents. Ethanol, propylene glycol and other low molecular alcohols, menthol, eucalyptol, limonene and many other terpenes, low molecular fatty acids such as capric acid and dimethyl sulfoxide are named exemplarily as typical additives in transdermal therapeutic systems which represent a risk factor for classical printing technology. Surprisingly, not as to be expected by the expert, a disadvantageous change of drug content occurs upon the influence of temperature.

Particularly, by application of modern printing tools and machinery, impairment of drug content is practically excluded at short contact times.

The invention is represented in FIG. 1 in detail. However, instead of the diffusion matrix (2) shown, other typical elements of such pharmaceutical forms of application and element groups (reservoirs, diffusion membranes, etc.) may be used without impairing the inventive solution.

BRIEF DESCRIPTION OF THE DRAWINGS

FIG. 1 shows a transdermal therapeutic system in cross-section with backing layer (1) divided up into printable thermoplastic layer (4) and diffusion-(and temperature-) barrier (5). The transdermal therapeutic system can also have a removable protecting layer (3).

The transdermal therapeutic system contains, therefore, the elements:

1. Backing layer, consisting of (4) and (5), with coding
2. Matrix
3. Removable protecting layer
4. Thermoplastic part of the backing layer with imprint
5. Diffusion barrier for the active agent (PETP).

In the present invention, coding is provided on the printable thermoplastic layer (4) of the backing layer. The coding consists of a locally different surface property, surface thickness or surface roughness of the backing layer. Coding on the backing layer may be generated by methods such as pressure, heat, ultrasound or abrasion. Such methods are known to those skilled in the art. The coding is typically performed after the transdermal therapeutic system has been formed.

We claim:

1. A transdermal therapeutic system comprising a backing layer and an active agent containing matrix layer, wherein the backing layer is provided with persistent information which consists of a coding formed by a locally different surface property, surface thickness or surface roughness of the backing layer, said backing layer consists of a laminate comprising an external layer and a layer facing the matrix, wherein the external layer is a low-melting thermoplastic material containing said information and the layer facing the skin is a higher melting thermoplastic material which protects the active agent containing matrix layer from damage during coding.

2. A method for manufacturing the transdermal therapeutic system according to claim 1, wherein the coding of the backing layer is performed after the completion of a process for preparing the transdermal therapeutic system, said coding is accomplished by the influence of pressure, heat, ultrasound or abrasion.

* * * * *